United States Patent [19]
Kateley

[11] Patent Number: 5,692,687
[45] Date of Patent: Dec. 2, 1997

[54] MEDICAL WASTE PROCESSING AND DISINFECTING APPARATUS

[76] Inventor: Richard D. Kateley, 113 Whispering Woods Hill, Guilford, Conn. 06457

[21] Appl. No.: 614,972

[22] Filed: Mar. 11, 1996

[51] Int. Cl.⁶ .................................................. B02C 19/12
[52] U.S. Cl. .................... 241/65; 241/100; 241/101.3; 241/606; 241/DIG. 37
[58] Field of Search ............... 241/606, 65, DIG. 37, 241/101.3, 100

[56] References Cited

U.S. PATENT DOCUMENTS

| | | | |
|---|---|---|---|
| 4,073,443 | 2/1978 | Danioni | 241/DIG. 37 X |
| 4,269,364 | 5/1981 | Moriconi et al. | 241/606 X |
| 4,531,437 | 7/1985 | Szablak et al. | 241/606 X |
| 4,889,290 | 12/1989 | Koffsky et al. | 241/606 X |
| 5,035,367 | 7/1991 | Nojima | 241/606 X |
| 5,064,124 | 11/1991 | Chang | 241/606 X |

FOREIGN PATENT DOCUMENTS

| | | | |
|---|---|---|---|
| 220413 | 8/1993 | Japan | 241/606 |

*Primary Examiner*—Mark Rosenbaum
*Attorney, Agent, or Firm*—Alfred E. Miller

[57] ABSTRACT

A medical waste handling device in which the medical waste material, including syringes, are ground and crushed in a grinding unit while being sanitized and subjected to a cold temperature of about −50° F. to make the waste material brittle, passing the fragmented waste material into a removable receptacle in a housing and in which the receptacle is further provided with a disinfectant to secondarily sanitize the medical waste material.

6 Claims, 4 Drawing Sheets

MEDICAL WASTE PROCESSING AND DISINFECTING APPARATUS

The present invention relates to the handling of medical waste by grinding and crushing medical waste products in a chilled container and thereafter discharging the fragments to a removable container, and disinfecting the same in said container.

BACKGROUND OF THE INVENTION

Hospitals, nursing homes and doctor's office's are faced with a mounting problem of the sanitary disposal of medical waste, some of which maybe infectious. The disposal of such waste in landfills is strictly controlled by government. Therefore, it is incumbent upon institutions and individual doctors to find a way of disposing of medical waste in a sanitary fashion.

It is known to burn such hospital or doctor's medical wastes in an incinerator. However, it is an inefficient operation at best, and requires additional equipment in order to insure that the combustion is complete and that the apparatus does not generate obnoxious odors and fumes as well as producing airborne disease producing organisms. Thus, it should become apparent that the incineration of medical waste, some of which is infectious, is not the most desirable method of treating the disposition of medical waste material.

A further troublesome aspect of this problem is the disposal of syringes wherein the rubber portions of the syringes, when disposed, are difficult to handle. They are not stable and tend to bounce in the disposal receptacle. Consequently, it is difficult to crush discarded syringes in a receptacle.

SUMMARY OF THE INVENTION

It is a feature of the present invention to provide a relatively small medical waste processing and disinfecting apparatus, which can be portable and in which a removable receptacle or container receives the pulverized and disinfected remnants of medical waste material, including syringes and medical staples.

It is a feature of the present invention to have a grinding unit for medical waste in a chamber that is chilled to about −50° F. and is provided with a disinfectant solution so that the brittle medical waste is crushed into fragments.

Another feature of the present invention is to provide a removable waste container in the housing of the disposal unit which is also chilled and provided with additional disinfectant solutions so that the fragments remaining are sanitized to a degree that the removable container can be disposed of in the manner of ordinary garbage or refuse.

A further aspect of the present invention is a removable container with an automatically closable opening when the container is removed from the medical waste grinding and disinfecting apparatus.

Another aspect of the present invention is to provide a medical waste disposal apparatus that is portable and which can be moved to any location in a hospital or doctor's office for use.

And still another object of the present invention is to provide a medical waste disposal apparatus that has indicating means on the housing alerting users when the disposable container is full.

The above and other objects, aspects and features of the invention will be apparent by reference to the following description of my invention and drawings.

DESCRIPTION OF THE PREFERRED EMBODIMENT

Figure 1:
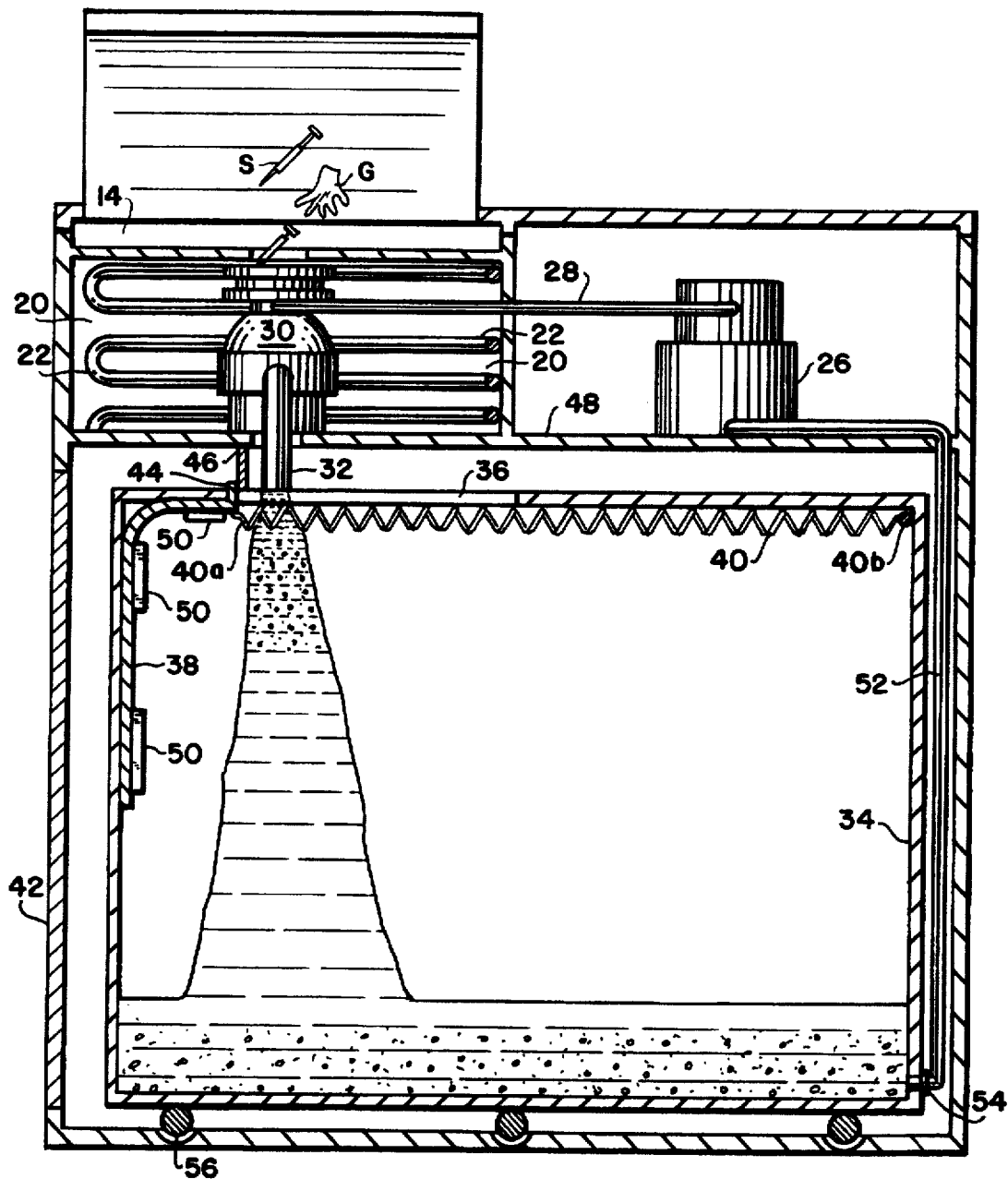
FIG. 1 is a sectional view of the medical waste processing and disinfecting apparatus constructed in accordance with my invention.

Referring to FIGS. 1–4, an on-site medical waste processing and disinfecting unit is shown referred to generally by the reference numeral 10 having a rectangular housing 12 provided with a top opening 14 and side opening 16. Opening 14 is closed by a lid 18. Top opening 14 permits the user to dispose of a variety of medical waste material in the unit or appliance 10. The medical waste material enters an upper chamber 20 which is provided with cooling coils 22 that are connected to a cooling unit having a compressor 24.

Figure 2:
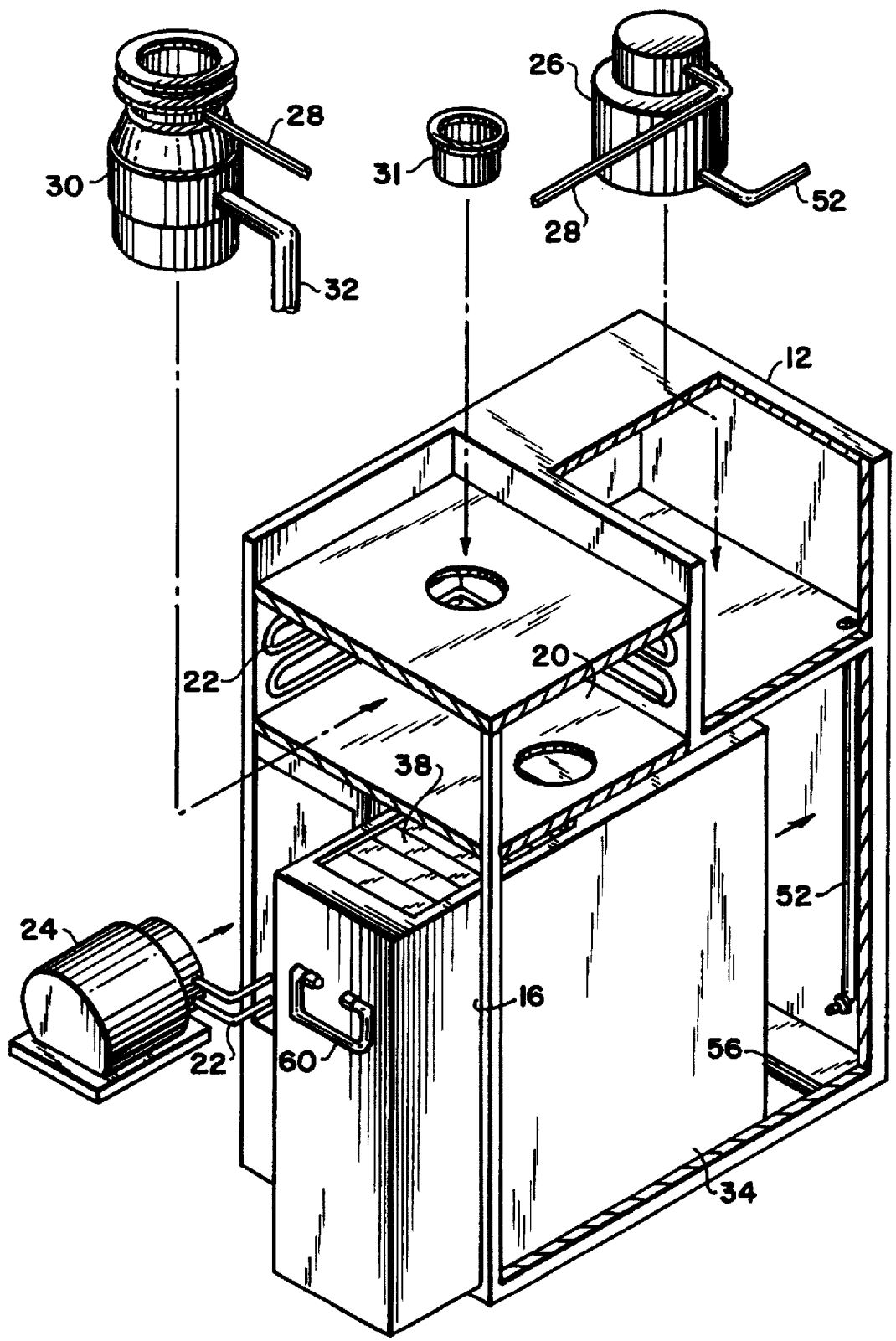
FIG. 2 is an exploded perspective view of the apparatus shown in FIG. 1 showing the container for the treated medical waste partially out of the housing of the apparatus.
Figure 3:
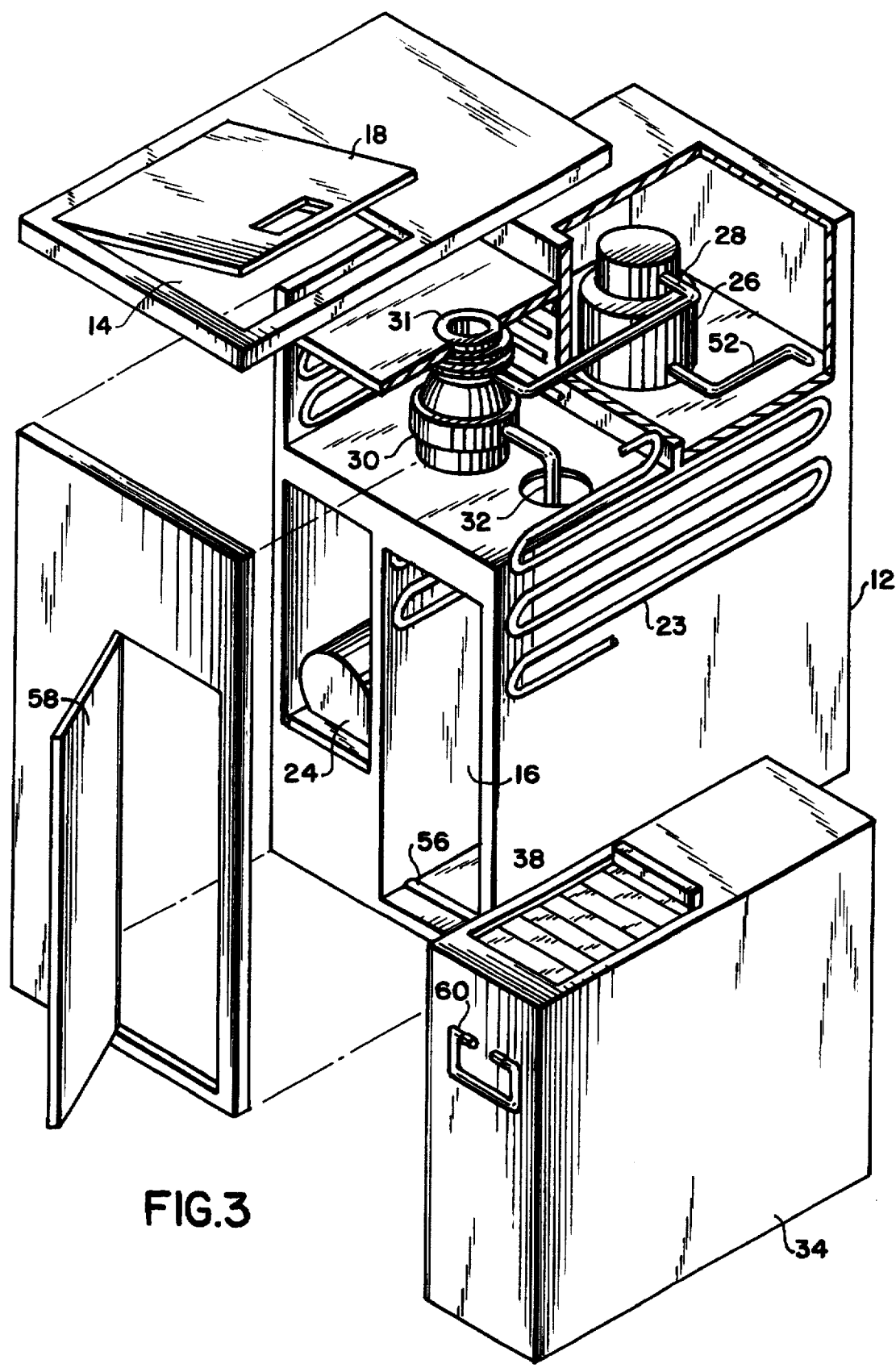
FIG. 3 is another exploded perspective view of the apparatus with the container removed entirely from the housing of the apparatus and FIG. 4 is a perspective view of the assembled apparatus as it appears in use.

A disinfectant pump 26 circulates a disinfectant, such as an ammonia-water mixture or glutaraldehyde through pipe 28 into and through containment ring 31 and grinding unit 30 that may have a constriction similar to a domestic kitchen disposal unit and having counter rotating cutter blades (not shown). Medical waste, such as syringes S and latex gloves G, are deposited in the top opening 14 and are chilled to a condition where the material becomes brittle so that the material can be more easily crushed in the grinding unit 30 and then into fragments while in a disinfectant solution. The remnants of the medical waste which has been sanitized with a disinfectant solution passes through pipe 32 by means of gravity into a removable container or receptacle 34 through a closable opening 36. The opening is provided with a cover 38 having a spring 40 which is connected at 40a to the back end of the cover at one end of the cover, and connected at the other end 40b to the underside of the top of receptacle 34. Thus, the cover 38 is spring-loaded, and is normally in a closed position, as shown in FIGS. 2 and 3. However, when the receptacle 34 is inserted through the opening 16 an upstanding flange 44 on the back end of the cover 38 engages a vertical post 46 depending from partition 48 of the housing 12 whereby the cover 38 is caused to move on tracks 50 to a substantially vertical position adjacent to an inner side of the receptacle 38, as seen in FIG. 1. When the cover is in the position shown in FIG. 1 the opening 36 of receptacle 34 is fully open, thus allowing the partially treated medical waste to fall into receptacle 34.

It should be noted that the disinfectant pump 26 has a pipe line 52 that is connected to receptacle 34 when the latter is fully inserted in the housing 12 through opening 54 in the rear of receptacle 34. FIG. 2 shows the pipe 52 prior to connection with the receptacle 34. When the connection is made, disinfectant is directed into the receptacle 34 in order to additionally sanitize the remnants and fragments of the medical waste treated in the appliance. The cooling coils 23 are shown adjacent to the opening 16 in the housing 12 for continuing the freezing of the medical waste in the receptacle 34 as it is further sanitized.

Figure 4:
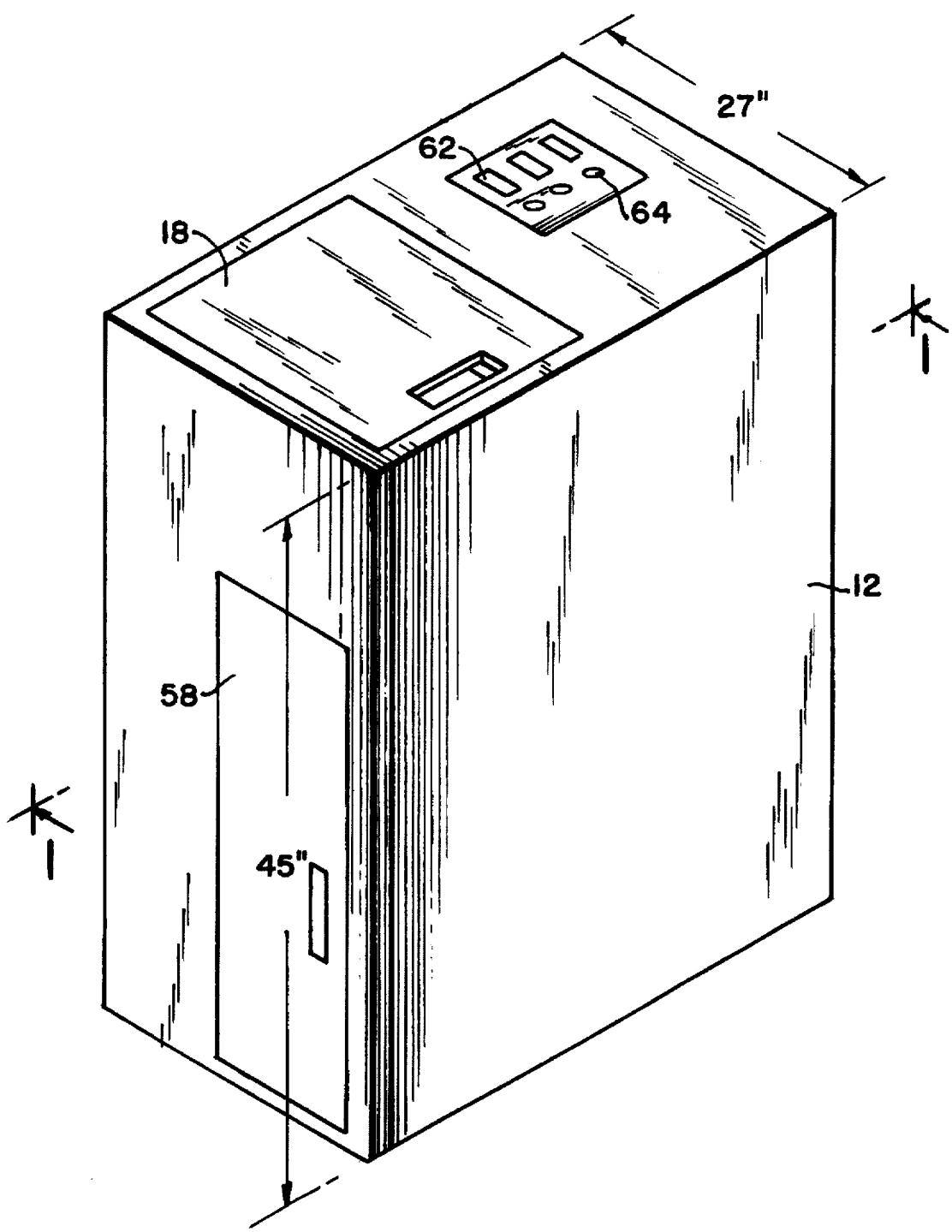

In order to further facilitate the insertion and removal of the receptacle 34 in the housing 12, spaced rollers 56 are provided, as seen in FIG. 1. The opening 16 in the side of the housing 12 is provided with a door 58 and receptacle 34 has a handle 60 so that the receptacle 34 can be easily removed. In addition, as seen in FIG. 4, the present appliance is provided with controls 62 on a control panel which includes colored lights 64 to indicate to the user when the unit can be used and also when the receptacle is full and should be replaced with an empty receptacle.

After the treatment procedure has been completed the on-site fractionated medical waste is sanitized to such a degree that it can be disposed of in the manner of ordinary garbage and refuse.

While the present invention has been described and shown with reference a preferred embodiment it is not intended to be limited by the present disclosure but should cover equivalents in accordance with the spirit and scope of the invention as defined in the following claims.

What I claim is:

1. A medical waste processing and disinfecting device comprising:
   (a) a housing having a top opening, a side opening, and a closable lid for said top opening,
   (b) a chamber adjacent to the top opening of said housing for recovering medical waste products,
   (c) means in said chamber for chilling said medical waste products to a temperature whereby said products become brittle;
   (d) a disinfectant pump and associated piping for delivering a disinfectant solution to the chamber and said medical waste products in said chamber,
   (e) a mechanical grinding unit in said chamber for grinding and crushing said medical waste products into fragments,
   (f) a removable receptacle insertable through the side opening of said housing, said receptacle having a top opening provided with a normally closed, spring-biased cover, co-acting means on said cover and housing for removing said cover from said top opening upon said receptacle being slid into said housing, said top opening being in communication with said chamber whereby fragments of medical waste products fall by gravity into the receptacle, and said cover being self-closing upon withdrawal of said receptacle from said housing and,
   (g) a pipe connected to said disinfectant pump for providing additional disinfectant solution to said receptacle when said receptacle is positioned within said housing.

2. A medical waste and processing device as claimed in claim 1 wherein said disinfectant is an ammonia and water solution.

3. A medical waste and processing device as claimed in claim 1 wherein said disinfectant is a glutaraldehyde solution.

4. A medical waste and processing device as claimed in claim 1 wherein said means for chilling includes a compressor which is capable of maintaining a temperature of at least −40° F. in both the grinding unit and in said removable receptacle.

5. The medical waste processing and disinfecting device as claimed in claim 1 further providing visual indicating means for alerting the user when the receptacle is filled.

6. A device as claimed in claim 1 wherein said temperature in the upper chamber is at least −40° F.

\* \* \* \* \*